US 12,409,312 B2

(12) United States Patent
Lucas et al.

(10) Patent No.: US 12,409,312 B2
(45) Date of Patent: Sep. 9, 2025

(54) DEVICE HOUSING FEATURES TO FACILITATE DAMAGE FREE GUIDEWIRE TRANSLATIONS

(71) Applicant: Boston Scientific Scimed Inc., Maple Grove, MN (US)

(72) Inventors: Jeffrey Lucas, Hopkins, MN (US); Lloyd Radman, Blaine, MN (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 406 days.

(21) Appl. No.: 17/988,977

(22) Filed: Nov. 17, 2022

(65) Prior Publication Data

US 2023/0149695 A1     May 18, 2023

Related U.S. Application Data

(60) Provisional application No. 63/280,345, filed on Nov. 17, 2021.

(51) Int. Cl.
*A61M 60/148* (2021.01)
*A61M 60/414* (2021.01)

(52) U.S. Cl.
CPC ........ *A61M 60/148* (2021.01); *A61M 60/414* (2021.01)

(58) Field of Classification Search
CPC .............. A61M 60/148; A61M 60/414; A61M 60/221; A61M 60/419; A61M 60/81; A61M 60/865; A61M 60/13
See application file for complete search history.

(56) References Cited

U.S. PATENT DOCUMENTS

| 5,527,159 A | 6/1996 | Bozeman, Jr. et al. |
| 5,692,882 A | 12/1997 | Bozeman, Jr. et al. |
| 5,947,892 A | 9/1999 | Benkowski et al. |
| 6,135,729 A | 10/2000 | Aber |
| 6,139,487 A | 10/2000 | Siess |
| 6,176,822 B1 | 1/2001 | Nix et al. |
| 6,248,091 B1 | 6/2001 | Voelker |
| 7,841,976 B2 | 11/2010 | McBride et al. |
| 7,927,068 B2 | 4/2011 | McBride et al. |
| 7,972,122 B2 | 7/2011 | Larose et al. |
| 8,376,707 B2 | 2/2013 | McBride et al. |

(Continued)

FOREIGN PATENT DOCUMENTS

| EP | 847767 B1 | 2/2005 |
| EP | 2301598 B1 | 7/2017 |

(Continued)

OTHER PUBLICATIONS

US 9,067,007 B2, 06/2015, Tanner et al. (withdrawn)

(Continued)

*Primary Examiner* — Paula J Stice
(74) *Attorney, Agent, or Firm* — Seager, Tufte & Wickhem LLP

(57) ABSTRACT

Various aspects of the present disclosure are directed towards apparatuses, systems, and methods that include a percutaneous circulatory support device. The percutaneous circulatory support device is used with a guidewire and may include a housing having a blood outlet aperture. The blood outlet aperture may include a channel that is configured to receive and support the guidewire.

20 Claims, 6 Drawing Sheets

(56) References Cited

U.S. PATENT DOCUMENTS

| | | |
|---|---|---|
| 8,591,393 B2 | 11/2013 | Walters et al. |
| 8,597,170 B2 | 12/2013 | Walters et al. |
| 8,684,904 B2 | 4/2014 | Campbell et al. |
| 8,721,517 B2 | 5/2014 | Zeng et al. |
| 8,814,776 B2 | 8/2014 | Hastie et al. |
| 8,992,163 B2 | 3/2015 | Mcbride et al. |
| 9,072,825 B2 | 7/2015 | Pfeffer et al. |
| 9,138,518 B2 | 9/2015 | Yuen et al. |
| 9,162,017 B2 | 10/2015 | Evans et al. |
| 9,308,302 B2 | 4/2016 | Zeng |
| 9,308,304 B2 | 4/2016 | Peters et al. |
| 9,327,067 B2 | 5/2016 | Zeng et al. |
| 9,364,592 B2 | 6/2016 | Mcbride et al. |
| 9,364,593 B2 | 6/2016 | Mcbride et al. |
| 9,381,288 B2 | 7/2016 | Schenck et al. |
| 9,402,942 B2 | 8/2016 | Hastie et al. |
| 9,421,311 B2 | 8/2016 | Tanner et al. |
| 9,446,179 B2 | 9/2016 | Keenan et al. |
| 9,675,740 B2 | 6/2017 | Zeng et al. |
| 9,717,833 B2 | 8/2017 | Mcbride et al. |
| 9,750,861 B2 | 9/2017 | Hastie et al. |
| 9,770,543 B2 | 9/2017 | Tanner et al. |
| 9,814,814 B2 | 11/2017 | Corbett et al. |
| 9,872,947 B2 | 1/2018 | Keenan et al. |
| 9,872,948 B2 | 1/2018 | Siess |
| 9,895,476 B2 | 2/2018 | Larose et al. |
| 9,907,890 B2 | 3/2018 | Muller |
| 9,956,332 B2 | 5/2018 | Larose et al. |
| 9,962,475 B2 | 5/2018 | Yuen et al. |
| 9,964,115 B2 | 5/2018 | Scheckel |
| 10,029,037 B2 | 7/2018 | Muller et al. |
| 10,039,872 B2 | 8/2018 | Zeng et al. |
| 10,071,192 B2 | 9/2018 | Zeng |
| 10,086,121 B2 | 10/2018 | Fitzgerald et al. |
| 10,105,475 B2 | 10/2018 | Muller |
| 10,117,980 B2 | 11/2018 | Keenan et al. |
| 10,149,932 B2 | 12/2018 | McBride et al. |
| 10,215,187 B2 | 2/2019 | McBride et al. |
| 10,232,099 B2 | 3/2019 | Peters et al. |
| 10,251,985 B2 | 4/2019 | Larose et al. |
| 10,251,986 B2 | 4/2019 | Larose et al. |
| 10,478,539 B2 | 11/2019 | Pfeffer et al. |
| 10,478,540 B2 | 11/2019 | Scheckel et al. |
| 10,525,178 B2 | 1/2020 | Zeng |
| 10,576,192 B2 | 3/2020 | Muller et al. |
| 10,576,193 B2 | 3/2020 | Tanner et al. |
| 10,617,808 B2 | 4/2020 | Hastie et al. |
| 10,709,829 B2 | 7/2020 | Muller |
| 10,709,830 B2 | 7/2020 | Tanner et al. |
| 10,737,008 B2 | 8/2020 | Corbett et al. |
| 10,765,789 B2 | 9/2020 | Zeng et al. |
| 10,780,208 B2 | 9/2020 | Siess et al. |
| 10,786,610 B2 | 9/2020 | Zeng |
| 10,799,624 B2 | 10/2020 | Pfeffer et al. |
| 10,842,921 B2 | 11/2020 | Siess et al. |
| 10,864,308 B2 | 12/2020 | Muller et al. |
| 10,864,309 B2 | 12/2020 | McBride et al. |
| 10,874,783 B2 | 12/2020 | Pfeffer et al. |
| 10,894,115 B2 | 1/2021 | Pfeffer et al. |
| 10,918,773 B2 | 2/2021 | Guo et al. |
| 10,918,774 B2 | 2/2021 | Stanfield et al. |
| 10,960,116 B2 | 3/2021 | Yuen et al. |
| 10,980,927 B2 | 4/2021 | Pfeffer et al. |
| 11,058,865 B2 | 7/2021 | Fitzgerald et al. |
| 11,123,539 B2 | 9/2021 | Pfeffer et al. |
| 11,129,978 B2 | 9/2021 | Pfeffer et al. |
| 11,167,124 B2 | 11/2021 | Pfeffer et al. |
| 11,229,786 B2 | 1/2022 | Zeng et al. |
| 11,235,138 B2 | 2/2022 | Gross-Hardt et al. |
| 11,253,693 B2 | 2/2022 | Pfeffer et al. |
| 11,260,213 B2 | 3/2022 | Zeng et al. |
| 11,273,301 B2 | 3/2022 | Pfeffer et al. |
| 11,305,105 B2 | 4/2022 | Corbett et al. |
| 11,311,712 B2 | 4/2022 | Zeng et al. |
| 11,338,124 B2 | 5/2022 | Pfeffer et al. |
| 11,357,967 B2 | 6/2022 | Zeng et al. |
| 11,400,276 B2 | 8/2022 | Chopra et al. |
| 11,497,896 B2 | 11/2022 | Tanner et al. |
| 11,511,101 B2 | 11/2022 | Hastie et al. |
| 11,517,736 B2 | 12/2022 | Earles et al. |
| 11,583,659 B2 | 2/2023 | Pfeffer et al. |
| 11,628,294 B2 | 4/2023 | Chopra et al. |
| 11,708,833 B2 | 7/2023 | McBride et al. |
| 11,754,075 B2 | 9/2023 | Schuelke et al. |
| 11,786,700 B2 | 10/2023 | Pfeffer et al. |
| 2008/0086027 A1* | 4/2008 | Siess ............ A61M 60/405 600/16 |
| 2008/0114339 A1 | 5/2008 | McBride et al. |
| 2009/0060743 A1 | 3/2009 | McBride et al. |
| 2017/0080189 A1 | 3/2017 | Tao et al. |
| 2017/0296725 A1 | 10/2017 | Peters et al. |
| 2018/0303990 A1 | 10/2018 | Siess et al. |
| 2018/0311423 A1 | 11/2018 | Zeng et al. |
| 2020/0038568 A1 | 2/2020 | Higgins et al. |
| 2021/0015982 A1 | 1/2021 | Kerkhoffs et al. |
| 2021/0038785 A1 | 2/2021 | Siess et al. |
| 2021/0077680 A1 | 3/2021 | Tanner et al. |
| 2021/0106810 A1 | 4/2021 | Pfeffer et al. |
| 2021/0268264 A1 | 9/2021 | Stotz et al. |
| 2021/0361926 A1 | 11/2021 | Corbett et al. |
| 2022/0134082 A1 | 5/2022 | Pfeffer et al. |
| 2023/0063798 A1 | 3/2023 | Edwards et al. |

FOREIGN PATENT DOCUMENTS

| | | |
|---|---|---|
| EP | 3352808 B1 | 9/2023 |
| JP | 2008516654 A | 5/2008 |
| JP | 2021526441 A | 10/2021 |
| WO | 0117851 A2 | 3/2001 |
| WO | 2022173977 A1 | 8/2022 |

OTHER PUBLICATIONS

International Search Report and Written Opinion for International Application No. PCT/US2022/050212, mailing date Mar. 13, 2023. (17 pages).

* cited by examiner

DEVICE HOUSING FEATURES TO FACILITATE DAMAGE FREE GUIDEWIRE TRANSLATIONS

CROSS REFERENCE TO RELATED APPLICATION

This application claims priority to Provisional Application No. 63/280,345, filed Nov. 17, 2021, which is herein incorporated by reference in its entirety.

TECHNICAL FIELD

The present disclosure relates to percutaneous circulatory support systems. More specifically, the disclosure relates to percutaneous circulatory support devices that are delivered to a patient's heart using a guidewire.

BACKGROUND

Percutaneous circulatory support devices can provide transient support for up to approximately several weeks in patients with compromised heart function or cardiac output. Such devices are typically delivered to a patient's heart using a guidewire, whereby the circulatory support device is coupled to and moved along the guidewire through the patient's vasculature until the device is in the proper position within the heart. Generally, circulatory support devices are coupled to a guidewire by feeding the proximal end of a guidewire, the distal end of which has already been inserted into a patient's vasculature, through an opening in the device. The proximal end of the guidewire is then passed through the device and exits the device via another opening. The device is then able to be moved along the length of guidewire to insert the device into the patient's vasculature and ultimately into the patient's heart. As the guidewire passes through the openings in the device or the device moves along the guidewire, the guidewire may be damaged because the device is typically made of a metal material, while the guidewire is composed of a softer material or contains a coating. For example, the coating of the guidewire may be removed by contact between the guidewire and a surface of one of the openings. The removal of the coating material may cause health complications or negatively affect the performance of the guidewire and/or device.

SUMMARY

In an Example 1, a percutaneous circulatory support device for use with a guidewire comprises a housing including an interior lumen, an exterior surface, a blood inlet, and a blood outlet that includes a blood outlet aperture, wherein the blood outlet aperture includes a channel extending from the interior lumen to the exterior surface of the housing, the channel configured to non-marringly receive and support the guidewire.

In an Example 2, the percutaneous circulatory support device of Example 1, the device further comprises an impeller disposed within the interior lumen, the impeller configured to rotate relative to the housing to cause blood to flow into the blood inlet, through the interior lumen of the housing, and out of the blood outlet, and a motor operatively coupled to the impeller, the motor configured to rotatably drive the impeller.

In an Example 3, the percutaneous circulatory support device of Example 1 or 2, wherein the blood outlet aperture is a first blood outlet aperture, the blood outlet includes a second blood outlet aperture, and the channel extends proximally beyond the second blood outlet aperture.

In an Example 4, the percutaneous circulatory support device of any one of Examples 1 to 3, wherein the channel includes a first end portion which is sloped.

In an Example 5, the percutaneous circulatory support device of any one of Examples 1 to 3, wherein the channel includes a first end portion which is rounded.

In an Example 6, the percutaneous circulatory support device of any one of Examples 1 to 5, wherein the channel includes a width greater than the guidewire.

In an Example 7, the percutaneous circulatory support device of any one of Examples 1 to 6, wherein the channel has a length of 0.025 to 0.375 inches.

In an Example 8, the percutaneous circulatory support device of any one of Examples 1 to 7, wherein the channel includes a substantially flat surface to support the guidewire.

In an Example 9, the percutaneous circulatory support device of any one of Examples 1 to 8, wherein the channel is located on a proximal portion of the blood outlet aperture.

In an Example 10, the percutaneous circulatory support device of any one of Examples 1 to 9, wherein the housing further comprises a first housing portion proximal of the channel, a second housing portion distal of the channel, wherein the first housing portion has a first diameter and the second housing portion has a second diameter, the first diameter being smaller than the second diameter, and a tapered housing portion that extends between the first housing portion and the second housing portion, the channel being located within the tapered housing portion.

In an Example 11, the percutaneous circulatory support device of Example 10, wherein the channel includes a first side wall and a second side wall, the first and second side walls configured to form a flared opening adjacent the first housing portion.

In an Example 12, a method for using a percutaneous circulatory support device comprises inserting a distal end of a guidewire into the vasculature of a patient, inserting a proximal end of the guidewire into a housing of the device, the housing comprising an interior lumen, an impeller within the interior lumen, an exterior surface, and a blood outlet that includes a blood outlet aperture, the blood outlet aperture includes a channel, the channel extending from the interior lumen to the exterior surface of the housing and configured to non-marringly receive and support the guidewire, passing the proximal end of the guidewire through the interior lumen of the housing, passing the proximal end of the guidewire adjacent to the impeller, and passing the proximal end of the guidewire through the channel of the blood outlet aperture such that the guidewire extends from the interior lumen to an exterior surface of the housing.

In an Example 13, the method of Example 12, wherein the channel is located on a proximal portion of the blood outlet aperture.

In an Example 14, the method of Example 13, wherein the blood outlet aperture is a first blood outlet aperture, the housing includes a second blood outlet aperture, and the channel extends proximally beyond the second blood outlet aperture.

In an Example 15, the method of any one of Examples 12 to 14, further comprising moving the device along the guidewire and inserting the device into the vasculature of the patient.

In an Example 16, a percutaneous circulatory support device for use with a guidewire, comprises a housing comprising an interior lumen, an exterior surface, a blood inlet, and a blood outlet that includes a blood outlet aperture, an impeller disposed within the interior lumen, the impeller configured to rotate relative to the housing to cause blood to flow into the blood inlet, through the interior lumen of the housing, and out of the blood outlet; and a motor operatively coupled to the impeller, the motor configured to rotatably drive the impeller, wherein the blood outlet aperture includes a channel extending from the interior lumen to the exterior surface of the housing, the channel configured to non-marringly receive and support the guidewire.

In an Example 17, the percutaneous circulatory support device of Example 16, wherein the blood outlet aperture is a first blood outlet aperture, the blood outlet includes a second blood outlet aperture, and the channel extends proximally beyond the second blood outlet aperture.

In an Example 18, the percutaneous circulatory support device of Example 16, wherein the channel includes a first end portion which is sloped.

In an Example 19, the percutaneous circulatory support device of Example 16, wherein the channel includes a first end portion which is rounded.

In an Example 20, the percutaneous circulatory support device of Example 16, wherein the channel includes a width greater than the guidewire.

In an Example 21, the percutaneous circulatory support device of Example 16, wherein the channel has a length of 0.025 to 0.375 inches.

In an Example 22, the percutaneous circulatory support device of Example 16, wherein the channel includes a substantially flat surface to support the guidewire.

In an Example 23, the percutaneous circulatory support device of Example 16, wherein the channel is located on a proximal portion of the blood outlet aperture.

In an Example 24, the percutaneous circulatory support device of Example 16, wherein the housing further comprises a first housing portion proximal of the channel, a second housing portion distal of the channel, wherein the first housing portion has a first diameter and the second housing portion has a second diameter, the first diameter being smaller than the second diameter, and a tapered housing portion that extends between the first housing portion and the second housing portion, the channel being located within the tapered housing portion.

In an Example 25, the percutaneous circulatory support device of Example 24, wherein the channel includes a first side wall and a second side wall, the first and second side walls configured to form a flared opening adjacent the first housing portion.

In an Example 26, a percutaneous circulatory support device for use with a guidewire comprises a housing comprising an interior lumen, an exterior surface, a blood inlet, and a blood outlet that includes a first blood outlet aperture and a second blood outlet aperture, an impeller disposed within the interior lumen, the impeller configured to rotate relative to the housing to cause blood to flow into the blood inlet, through the interior lumen of the housing, and out of the first and second blood outlet apertures, and a motor operatively coupled to the impeller, the motor configured to rotatably drive the impeller, wherein the first blood outlet aperture that includes a channel configured to non-marringly receive and support the guidewire, the channel extending from the interior lumen to the exterior surface of the housing and proximally beyond the second blood outlet aperture.

In an Example 27, the percutaneous circulatory support system of Example 26, wherein the channel includes a first end portion which is sloped.

In an Example 28, the percutaneous circulatory support system of Example 26, wherein the channel includes a first end portion which is rounded.

In an Example 29, the percutaneous circulatory support system of Example 26, wherein the channel includes a substantially flat surface to support the guidewire.

In an Example 30, the percutaneous circulatory support system of Example 26, wherein the housing further comprises a first housing portion proximal of the channel, a second housing portion distal of the channel, wherein the first housing portion has a first diameter and the second housing portion has a second diameter, the first diameter being smaller than the second diameter, and a tapered housing portion that extends between the first housing portion and the second housing portion, the channel being located within the tapered housing portion.

In an Example 31, the percutaneous circulatory support device of Example 30, wherein the channel includes a first side wall and a second side wall, the first and second side walls configured to form a flared opening adjacent the first housing portion.

In an Example 32, a method for using a percutaneous circulatory support device, comprises inserting a distal end of a guidewire into the vasculature of a patient, inserting a proximal end of the guidewire into a housing of the device, the housing comprising an interior lumen, an impeller within the interior lumen, an exterior surface, and a blood outlet that includes a blood outlet aperture, the blood outlet aperture includes a channel, the channel extending from the interior lumen to the exterior surface of the housing and configured to non-marringly receive and support the guidewire, passing the proximal end of the guidewire through the interior lumen of the housing, passing the proximal end of the guidewire adjacent to the impeller, and passing the proximal end of the guidewire through the channel of the blood outlet aperture such that the guidewire extends from the interior lumen to an exterior surface of the housing.

In an Example 33, the method of Example 32, wherein the channel is located on a proximal portion of the blood outlet aperture.

In an Example 34, the method of Example 33, wherein the blood outlet aperture is a first blood outlet aperture, the housing includes a second blood outlet aperture, and the channel extends proximally beyond the second blood outlet aperture.

In an Example 35, the method of Example 32, further comprising moving the device along the guidewire and inserting the device into the vasculature of the patient.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
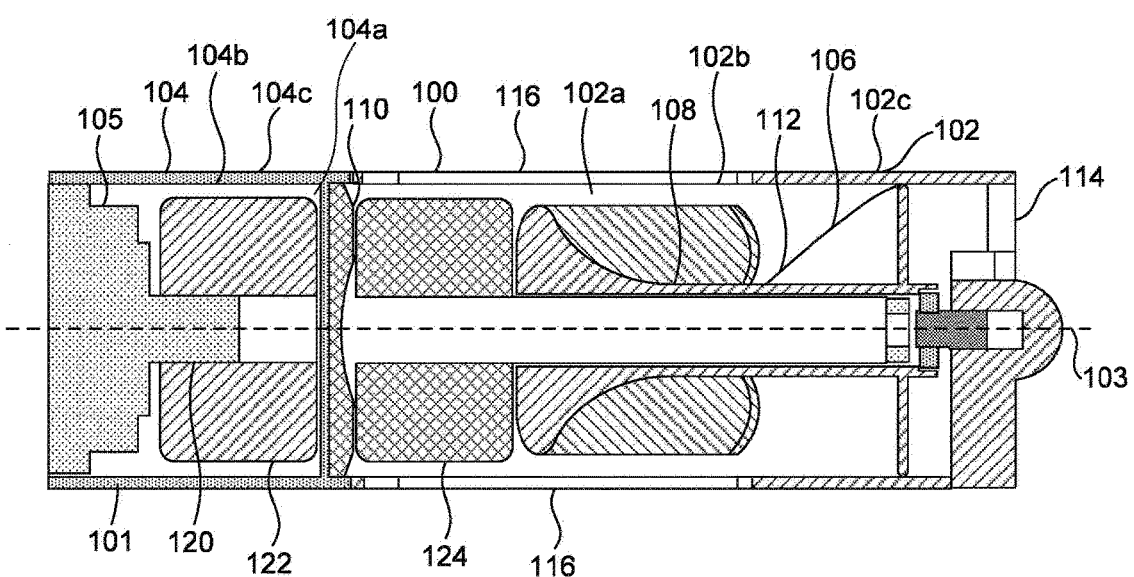
FIG. 1 is a side sectional view of an illustrative mechanical circulatory support device (also referred to herein, interchangeably, as a "blood pump"), in accordance with embodiments of the subject matter disclosed herein.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 depicts a partial side sectional view of an illustrative percutaneous circulatory support device 100 (also referred to herein, interchangeably, as a "blood pump") in accordance with embodiments of the subject matter disclosed herein. The device 100 may form part of a percutaneous circulatory support system, together with a guidewire (shown elsewhere) and an introducer sheath (shown elsewhere). More specifically, the guidewire and the introducer sheath may facilitate percutaneously delivering the device 100 to a target location within a patient, such as within the patient's heart. Alternatively, the device 100 may be delivered to a different target location within a patient.

With continued reference to FIG. 1, the device 100 generally includes a housing 101 that includes an impeller housing 102 and a motor housing 104. In some embodiments, the impeller housing 102 and the motor housing 104 may be integrally or monolithically constructed. In other embodiments, the impeller housing 102 and the motor housing 104 may be separate components configured to be removably or permanently coupled. In some embodiments, the blood pump 100 may lack a separate motor housing 104 and the impeller housing 102 may be coupled directly to the motor 105 described below, or the motor housing 104 may be integrally constructed with the motor 105 described below. Impeller housing 102 includes an interior lumen 102a, an interior surface 102b, and an exterior surface 102c. Similarly, the motor housing 104 includes an interior lumen 104a, an interior surface 104b, and an exterior surface 104c. Center axis 103 passes longitudinally through the housing 101.

The impeller housing 102 carries an impeller assembly 106 therein. The impeller assembly 106 includes an impeller shaft 108 that is rotatably supported by at least one bearing, such as a bearing 110. The impeller assembly 106 also includes an impeller 112 that rotates relative to the impeller housing 102 to drive blood through the device 100. More specifically, the impeller 112 causes blood to flow from a blood inlet 114 formed on the impeller housing 102, through the impeller housing 102, and out of a blood outlet 116 formed on the impeller housing 102. In some embodiments and as illustrated, the impeller shaft 108 and the impeller 112 may be separate components, and in other embodiments the impeller shaft 108 and the impeller 112 may be integrated.

In some embodiments and as described in more detail below, the inlet 114 and/or the outlet 116 may each include multiple apertures (see e.g., FIGS. 2-4). In other embodiments, the inlet 114 and/or the outlet 116 may each include a single aperture. In some embodiments and as illustrated, the inlet 114 may be formed on an end portion of the impeller housing 102 and the outlet 116 may be formed on a side portion of the impeller housing 102. In other embodiments, the inlet 114 and/or the outlet 116 may be formed on other portions of the impeller housing 102. In some embodiments, the impeller housing 102 may couple to a distally extending cannula (not shown), and the cannula may receive and deliver blood to the inlet 114.

With continued reference to FIG. 1, the motor housing 104 carries a motor 105, and the motor 105 is configured to rotatably drive the impeller 112 relative to the impeller housing 102. In the illustrated embodiment, the motor 105 rotates a drive shaft 120, which is coupled to a driving magnet 122. Rotation of the driving magnet 122 causes rotation of a driven magnet 124, which is connected to and rotates together with the impeller assembly 106. More specifically, in embodiments incorporating the impeller shaft 108, the impeller shaft 108 and the impeller 112 are configured to rotate with the driven magnet 124. In other embodiments, the motor 105 may couple to the impeller assembly 106 via other components.

In some embodiments, a controller (not shown) may be operably coupled to the motor 105 and configured to control the motor 105. In some embodiments, the controller may be disposed within the motor housing 104. In other embodiments, the controller may be disposed outside of the motor housing 104 (for example, in an independent housing, etc.). In some embodiments, the controller may include multiple components, one or more of which may be disposed within the motor housing 104. According to embodiments, the controller may be, may include, or may be included in one or more Field Programmable Gate Arrays (FPGAs), one or more Programmable Logic Devices (PLDs), one or more Complex PLDs (CPLDs), one or more custom Application Specific Integrated Circuits (ASICs), one or more dedicated processors (e.g., microprocessors), one or more Central Processing Units (CPUs), software, hardware, firmware, or any combination of these and/or other components. Although the controller is referred to herein in the singular, the controller may be implemented in multiple instances, distributed across multiple computing devices, instantiated within multiple virtual machines, and/or the like. In other embodiments, the motor 105 may be controlled in other manners.

Figure 2A:
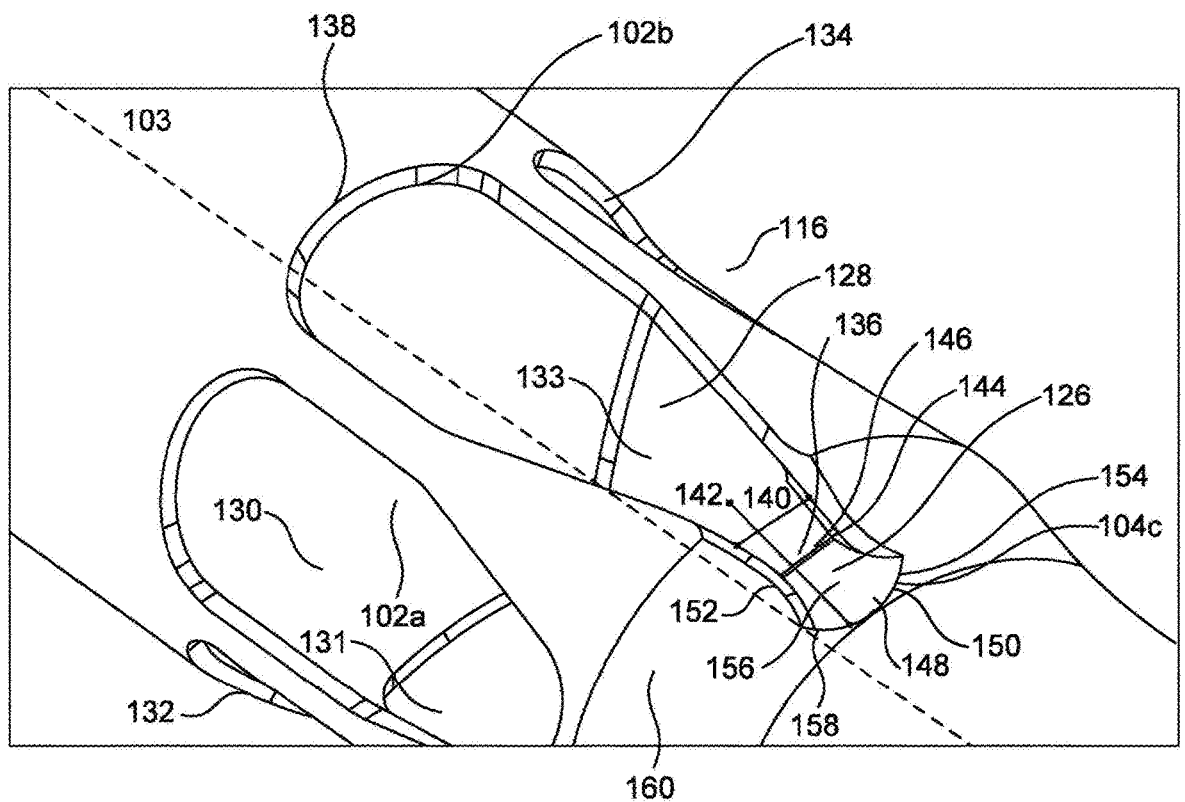
FIG. 2A is a perspective view of the mechanical circulatory support device of FIG. 1, in accordance with embodiments of the subject matter disclosed herein.

With continued reference to FIG. 1 and additional reference to FIG. 2A, the device 100 facilitates passage of a guidewire (shown elsewhere) through device 100 by the incorporation of a channel 126 in a blood outlet aperture 128 of the blood outlet 116. As described above, the blood outlet 116 may include more than one aperture, for example as shown in FIG. 2A, the blood outlet 116 includes six blood outlet apertures 128, 130, 131, 132, 133, and 134. As shown in FIG. 2A, the blood outlet aperture 128 includes a proximal portion 136 and a distal portion 138. In some embodiments and as shown in FIG. 2A, the channel 126 is located on the proximal portion 136 of the blood outlet aperture 128. In other embodiments, the channel 126 could be located on other portions of a blood outlet aperture, for example on the distal portion 138. As shown in FIG. 2A, the channel 126 extends from the blood outlet aperture 128 in a proximal direction. As also shown in FIG. 2A, the channel 126 extends proximally beyond each of the other blood outlet apertures 130, 131, 132, 133, and 134, thus indicating to a user that a guidewire should be passed through the blood outlet aperture 128 rather than the other blood outlet apertures 130, 131, 132, 133, and 134. Additional indicators, such as markings or lettering, may be placed near the channel 126 to indicate the proper location of the guidewire. The channel 126 has a width 140 and a length 142. The width 140 is generally no narrower than the width of the guidewire. In some embodiments, the length 142 may vary from 0.025 inches to 0.375 inches.

Figure 2B:
FIG. 2B is a perspective view of an illustrative blood outlet aperture and channel, in accordance with embodiments of the subject matter disclosed herein.
Figure 2C:
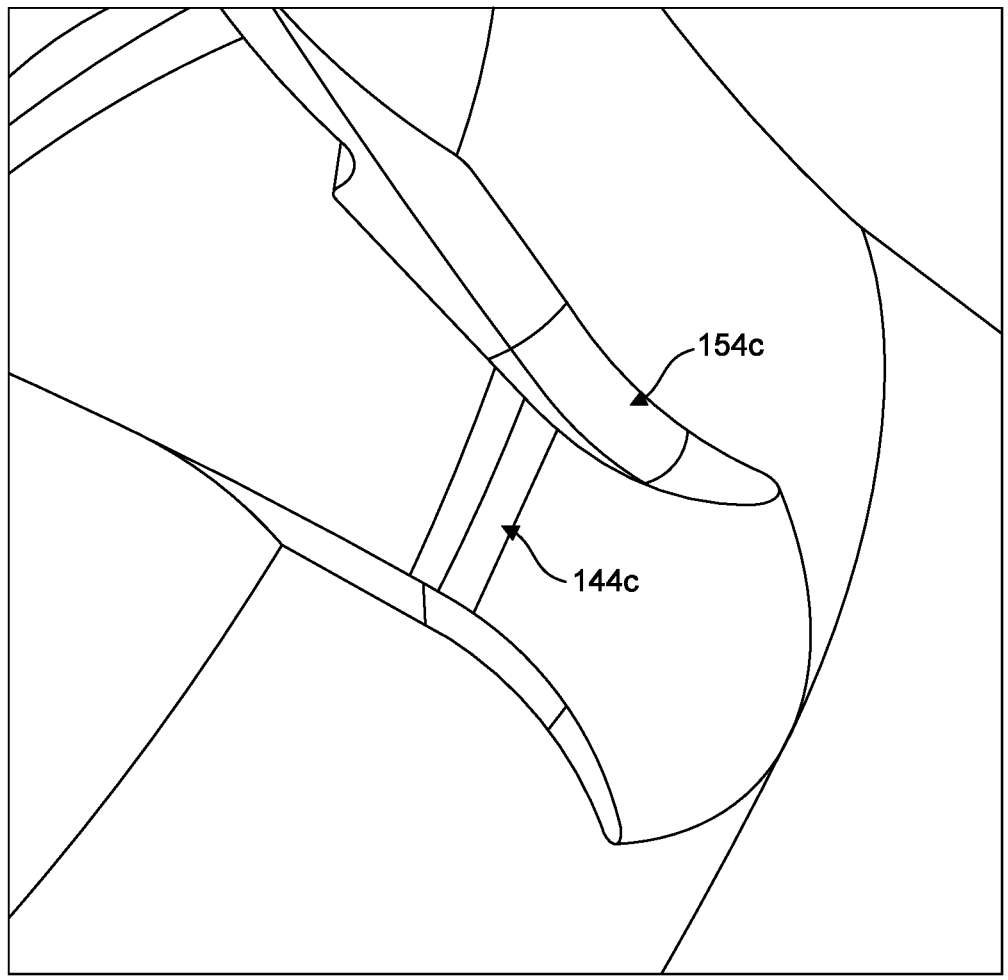
FIG. 2C is a perspective view of an illustrative blood outlet aperture and channel, in accordance with embodiments of the subject matter disclosed herein.

In the embodiment in FIGS. 2A-C, the channel 126 includes a first end portion 144 at the distal end 146 of the channel 126, that is, where the channel 126 meets interior surface 102b. Similarly, in the embodiment in FIGS. 2A-C, the channel 126 also includes a second end portion 148 at the proximal end 150 of the channel 126, where the channel 126 meets the exterior surface 104c. FIG. 2B illustrates a first end portion 144b that has not been sloped, beveled, rounded, or otherwise mechanically altered to smooth the first end portion 144. In contrast, in some embodiments, the first end portion 144 and/or second end portion 148 may be sloped, beveled, rounded, or otherwise mechanically altered to smooth the first end portion 144 and second end portion 148. For example, as shown in FIG. 2C, first end portion 144c is rounded to smooth the first end portion 144c. In some embodiments, channel 126 may include fewer or additional edges or surfaces than shown in FIGS. 2A-C, and some or all of such edges or surfaces may be smoothed through sloping, beveling, rounding, or other mechanical alteration. As further shown in FIGS. 2A-C, in some embodiments, the channel 126 includes a first side wall 152 and a second side wall 154, separated by the width 140, both of which extend along the length 142 and flare away from each other to form a flared opening 158 adjacent to the distal end 146 of the channel 126. The flared opening 158 may be, for example, at most 120 degrees wide. In some embodiments, the first side wall 152 and the second wall 154 may be sloped, beveled, rounded, or otherwise mechanically altered to smooth the surfaces of the first side wall 152 and a second side wall 154. For example, as shown in FIG. 2C, the second wall 154c is rounded. In other embodiments, the first side wall 152 and the second wall 154 may remain unaltered, as shown by second wall 154b in FIG. 2B.

As shown in FIGS. 2A-C and 3, the channel 126 also includes a substantially flat surface 156 extending between the end portions 144, 148 and the side walls 152, 154. Although the surface 156 may be slightly angled or tapered from the proximal end 150 and the distal end 146, the surface 156 is substantially flat to support the guidewire 200 along the channel 126 in the embodiment shown in FIG. 2 and FIG. 3. The guidewire 200 includes a distal end (not shown) and a proximal end 202, and may be composed of one or more metals, one or more plastics, composites, or the like. In some embodiments, the guidewire 200 may include a coating (not shown) that facilitates trackability within patient vasculature and reduces friction while advancing the device 100 over the guidewire 200 or while advancing the guidewire 200 through device 100. Such coatings may include PTFE, polymer coatings, or ceramic coatings through chemical vapor deposition processes such as atomic layer deposition.

In traditional circulatory support devices, as a guidewire is passed through the openings a circulatory support device, or the device moves along a guidewire, the guidewire may be damaged by contact between the guidewire and the device housing. For example, if the housing is made of a metal material, and the guidewire is composed of a softer material or contains a coating, the guidewire may be damaged, or the coating on the guidewire may be scraped off, during contact with relatively abrupt housing surfaces. Also, in traditional circulatory support devices, the guidewire may be bent at a relatively large angle or angles as the guidewire transitions from the interior to the exterior of the device housing.

In contrast to traditional devices, the likelihood of damage is substantially decreased with the device 100 due to the guidewire 200 passing through the channel 126. In particular, the above-described features of the channel 126 substantially reduce the chances that a coating on the guidewire 200 will be scraped off or damaged. In addition, the above-described features of the channel 126 minimize the amount that the guidewire 200 is deformed or bent as it transitions from the interior lumen 102a of the impeller housing 102 to the exterior surface 104c of the motor housing 104, providing the guidewire 200 with a flatter profile, and thus advantageously taking up less space within the introducer sheath 300, as shown in FIG. 4. Also, the flatter profile of the guidewire 200 facilitates easier movement of the device 100 along the guidewire 200, including through the introducer sheath 300 and the blood vessel V.

The above-described features of the channel 126 facilitate non-marringly receiving and supporting the guidewire 200 as the guidewire 200 passes through the blood outlet aperture 128. In particular, the channel 126 in the blood outlet aperture 128 provides a relatively smooth surface for the guidewire 200 to pass from the interior lumen 102a of the impeller housing 102 to the exterior surface 104c of the motor housing 104, as shown in FIG. 3. By incorporating the sloped, beveled, rounded, or otherwise modified first and second end portions 144, 148, the first and second side walls 152, 154, as well as the flared opening 152 and the substantially flat surface 156, the likelihood that the guidewire 200 will be damaged as the guidewire 200 passes through the blood outlet aperture 128, or when the device 100 is moved along the guidewire 200, is diminished as compared to other blood outlet apertures, such as the blood outlet apertures 130, 131, 132, 133, and 134, that do not include such features. For example, the channel 126 reduces the likelihood that a coating on the surface of the guidewire 200 is scraped off when the guidewire 200 passes through the blood outlet aperture 128, or when the device 100 is moved along the guidewire 200.

Figure 3:
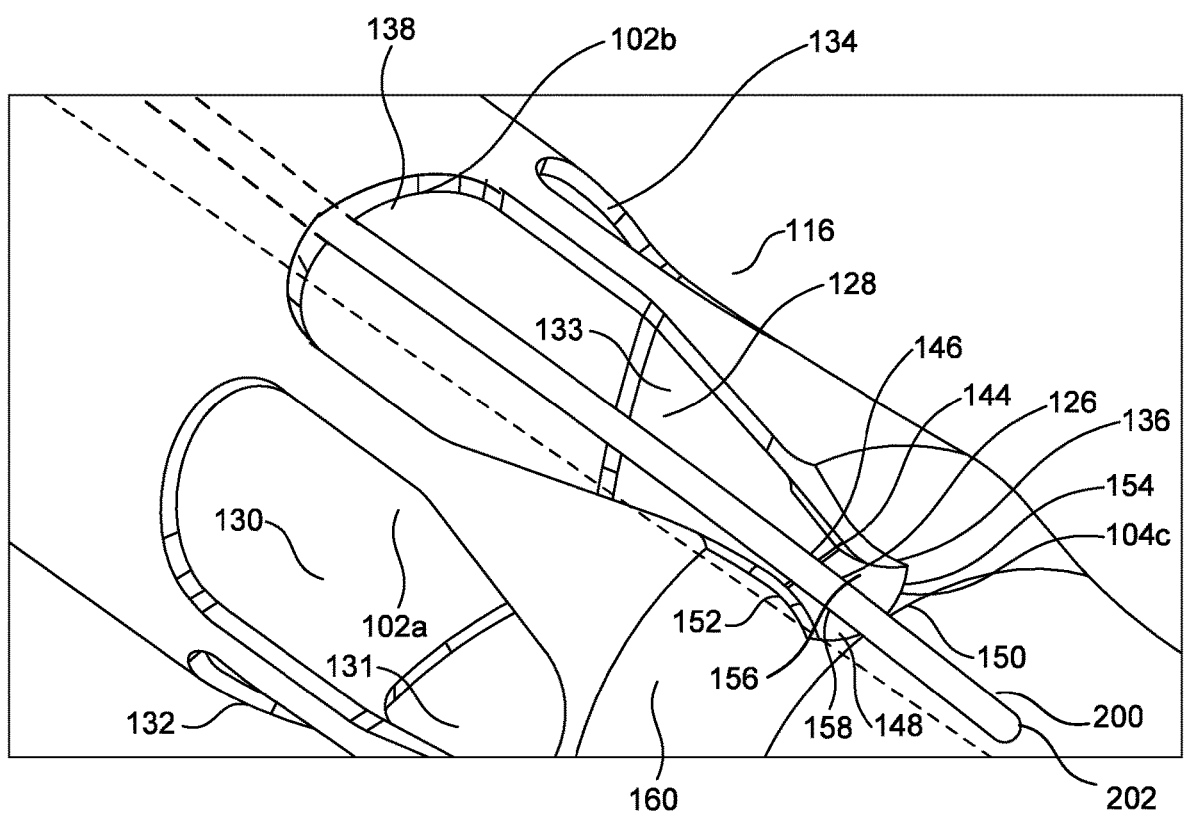
FIG. 3 is a perspective view of the mechanical circulatory support device of FIG. 1 and further illustrating a guidewire, in accordance with embodiments of the subject matter disclosed herein

In addition, the above-described features of the channel 126 minimize the amount that the guidewire 200 deforms or bends as the guidewire 200 passes from the interior lumen 102a of the impeller housing 102 to the exterior surface 104c of the motor housing 104, as shown in FIG. 3. Stated another way, by lengthening the transition area from the interior lumen 102a of the impeller housing 102 to the exterior surface 104c of the motor housing 104, the guidewire 200 assumes a flatter profile as compared to a guidewire transitioning in another blood outlet aperture, such as the blood outlet apertures 130, 131, 132, 133, and 134 that do not include a feature like the channel 126. As noted above, a flatter profile of the guidewire allows the guidewire to take up less space within the introducer sheath 300 and also permits easier movement of the device 100 along the guidewire 200.

With continued reference to FIGS. 2A-C and 3, in some embodiments, the impeller housing 102 has an outer diameter that is larger than the outer diameter of the motor housing 104. In alternative embodiments, the outer diameter of the impeller housing 102 may be substantially equal to the outer diameter of the motor housing 104, for example when impeller housing 102 and motor housing 104 are integrally or monolithically constructed. In still other embodiments, the outer diameter of the motor housing 104 may be larger than the outer diameter of the impeller housing 102. As shown in FIGS. 2A-C and 3, a tapered housing portion 160 extends between the impeller housing 102 and the motor housing 104. The tapered housing portion 160 creates a smooth transition along the housing 101 from the larger outer diameter of the impeller housing 102 to the relatively smaller outer diameter of the motor housing 104. As shown in FIG. 2A-C and FIG. 3, the channel 126 is located in the tapered housing portion 160 and is configured to facilitate the passage of the guidewire 200 from the interior lumen 102a of the impeller housing 102 to the exterior surface 104c of the motor housing 104. More specifically, in the embodiment shown in FIG. 2A-C and FIG. 3 the channel 126 is designed to minimize the amount that the guidewire 200 deforms or bends as the guidewire 200 passes from the interior lumen 102a of the impeller housing 102 to the exterior surface 104c of the motor housing 104. Stated differently, and illustrated in FIGS. 3 and 4, when the channel 126 is incorporated into a device 100 with a tapered housing portion 160, the guidewire 200 extends along the exterior surface 104c of the motor housing 104, passes through the blood outlet aperture 128 and into the interior lumen 102a of the impeller housing 102, while maintaining the same or similar distance from the center axis 103 of the housing 101.

In other embodiments, other portions besides the proximal portion 136 of the blood outlet 128 aperture may include a channel or similar structure for non-marringly receiving and supporting a guidewire. For example, the distal portion 138 of the blood outlet aperture 128 may include a channel or similar structure for non-marringly receiving and supporting a guidewire. In such an embodiment, the interior surface 102b of the impeller housing 102 at the distal portion 138 may be configured receive a guidewire, such as by the inclusion of a feature similar to the channel 126 described above. In other embodiments, the interior surface 102b of the impeller housing 102 at the distal portion 138 may be modified, sculpted, rounded, or otherwise configured to non-marringly receive and support a guidewire. In addition, in other embodiments, portions of the entirety of a blood outlet aperture may be treated with a coating or surface treatment to prevent damage to a guidewire. In still other embodiments, other apertures, such one or more of the apertures of the blood inlet 114, may include a channel, such as the channel 126, or similar structure for non-marringly receiving and supporting a guidewire.

Figure 4:
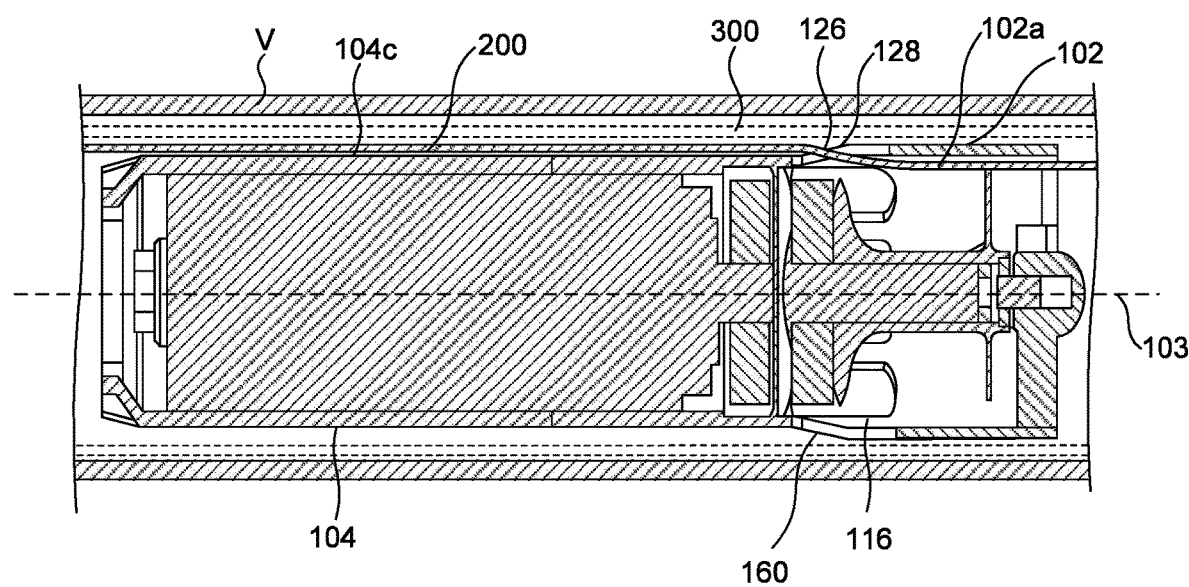
FIG. 4 is a side sectional view of the mechanical circulatory support device of FIG. 1 further illustrating a guidewire, introducer sheath, and blood vessel.

FIGS. 2A-C, 3, and 4 facilitate explanation of the method by which the blood pump 100 is used with the guidewire 200 and the advantages provided by the above-described features of the housing 101, including the channel 126. In an exemplary procedure, an introducer sheath 300 is inserted into the blood vessel (not shown), and the guidewire 200 is inserted through the introducer sheath 300 such that the proximal end 202 of the guidewire 200 is located outside the introducer sheath 300 and outside of the patient's body. The distal end (not shown) of the guidewire 200 is disposed distally from the introducer sheath 300 and located within the patient's vasculature, for example in the left ventricle of the heart. The blood pump 100 is then coupled to the guidewire 200 by feeding the proximal end 202 of the guidewire 200 through an opening in blood pump 100, such as the blood inlet 114. The proximal end 202 of the guidewire 200 is then passed through the housing 101, for example through the interior lumen 102a of the impeller housing 102, past the impeller 112, and exits the blood pump 100 via another opening, such as the blood outlet 116, and in particular and as shown in FIGS. 3 and 4, through the blood outlet aperture 128. As the guidewire 200 passes through the blood outlet aperture 128, the guidewire 200 is received and supported by the channel 126, thereby inhibiting damage to the guidewire 200 as it contacts the housing 101. FIG. 4 in particular illustrates the guidewire 200 extending proximally from the blood outlet aperture 128, including along the exterior surface 104c of the motor housing 104 and within the introducer sheath 300 and blood vessel V. Once coupled to the guidewire 200, the blood pump 100 is able to be moved along the length of the guidewire 200, through the introducer sheath 300 to insert the device 100 into the blood vessel V and ultimately into the patient's heart.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A percutaneous circulatory support device for use with a guidewire, comprising:
   a housing comprising an interior lumen, an exterior surface, a blood inlet, and a blood outlet that includes a blood outlet aperture;
   an impeller disposed within the interior lumen, the impeller configured to rotate relative to the housing to cause blood to flow into the blood inlet, through the interior lumen of the housing, and out of the blood outlet; and
   a motor operatively coupled to the impeller, the motor configured to rotatably drive the impeller, wherein the blood outlet aperture includes a channel extending from the interior lumen to the exterior surface of the housing, the channel having a tapered surface along the exterior surface of the housing proximal of the blood outlet aperture, the channel configured to non-marringly receive and support the guidewire.

2. The percutaneous circulatory support device of claim 1, wherein the blood outlet aperture is a first blood outlet aperture, the blood outlet includes a second blood outlet aperture, and the channel extends proximally beyond the second blood outlet aperture.

3. The percutaneous circulatory support device of claim 1, wherein the channel includes a first end portion which is sloped.

4. The percutaneous circulatory support device of claim 1, wherein the channel includes a first end portion which is rounded.

5. The percutaneous circulatory support device of claim 1, wherein the channel includes a width greater than the guidewire.

6. The percutaneous circulatory support device of claim 1, wherein the channel has a length of 0.025 to 0.375 inches.

7. The percutaneous circulatory support device of claim 1, wherein the channel includes a substantially flat surface to support the guidewire.

8. The percutaneous circulatory support device of claim 1, wherein the channel is located on a proximal portion of the blood outlet aperture.

9. The percutaneous circulatory support device of claim 1, wherein the housing further comprises:

a first housing portion proximal of the channel;
a second housing portion distal of the channel;
wherein the first housing portion has a first diameter and the second housing portion has a second diameter, the first diameter being smaller than the second diameter; and
a tapered housing portion that extends between the first housing portion and the second housing portion, the channel being located within the tapered housing portion.

10. The percutaneous circulatory support device of claim 9, wherein the channel includes a first side wall and a second side wall, the first and second side walls configured to form a flared opening adjacent the first housing portion.

11. A percutaneous circulatory support device for use with a guidewire, comprising:
a housing comprising an interior lumen, an exterior surface, a blood inlet, and a blood outlet that includes a first blood outlet aperture and a second blood outlet aperture;
an impeller disposed within the interior lumen, the impeller configured to rotate relative to the housing to cause blood to flow into the blood inlet, through the interior lumen of the housing, and out of the first and second blood outlet apertures; and
a motor operatively coupled to the impeller, the motor configured to rotatably drive the impeller, wherein the first blood outlet aperture includes a channel configured to non-marringly receive and support the guidewire, the channel extending from the interior lumen to the exterior surface of the housing and proximally beyond the second blood outlet aperture, the channel having a tapered surface along the exterior of the housing proximal of the blood outlet aperture.

12. The percutaneous circulatory support system of claim 11, wherein the channel includes a first end portion which is sloped.

13. The percutaneous circulatory support system of claim 11, wherein the channel includes a first end portion which is rounded.

14. The percutaneous circulatory support system of claim 11, wherein the channel includes a substantially flat surface to support the guidewire.

15. The percutaneous circulatory support system of claim 11, wherein the housing further comprises:
a first housing portion proximal of the channel;
a second housing portion distal of the channel;
wherein the first housing portion has a first diameter and the second housing portion has a second diameter, the first diameter being smaller than the second diameter; and
a tapered housing portion that extends between the first housing portion and the second housing portion, the channel being located within the tapered housing portion.

16. The percutaneous circulatory support device of claim 15, wherein the channel includes a first side wall and a second side wall, the first and second side walls configured to form a flared opening adjacent the first housing portion.

17. A method for using a percutaneous circulatory support device, comprising:
inserting a distal end of a guidewire into a vasculature of a patient;
inserting a proximal end of the guidewire into a housing of the device, the housing comprising an interior lumen, an impeller within the interior lumen, an exterior surface, and a blood outlet that includes a blood outlet aperture, the blood outlet aperture includes a channel, the channel extending from the interior lumen to the exterior surface of the housing proximal of the blood outlet aperture, having a tapered surface along the exterior surface of the housing, and configured to non-marringly receive and support the guidewire;
passing the proximal end of the guidewire through the interior lumen of the housing;
passing the proximal end of the guidewire adjacent to the impeller; and
passing the proximal end of the guidewire through the channel of the blood outlet aperture such that the guidewire extends from the interior lumen to an exterior surface of the housing.

18. The method of claim 17, wherein the channel is located on a proximal portion of the blood outlet aperture.

19. The method of claim 18, wherein the blood outlet aperture is a first blood outlet aperture, the housing includes a second blood outlet aperture, and the channel extends proximally beyond the second blood outlet aperture.

20. The method of claim 17, further comprising moving the device along the guidewire and inserting the device into the vasculature of the patient.

* * * * *